United States Patent [19]

Howell

[11] 4,010,750
[45] Mar. 8, 1977

[54] PARENTERAL FLUID ADMINISTRATION SETS
[76] Inventor: William L. Howell, 3615 Macomb St., Washington, D.C. 20016
[22] Filed: Feb. 6, 1976
[21] Appl. No.: 656,009
[52] U.S. Cl. .................. 128/214 C; 128/214 D; 128/228; 137/135; 222/416
[51] Int. Cl.[2] .......................... A61M 5/16
[58] Field of Search ....... 128/214 R, 214 C, 214 D, 128/214.2, 228; 137/130, 131, 135, 578; 222/67, 204, 416

[56] References Cited

UNITED STATES PATENTS

| | | | |
|---|---|---|---|
| 2,542,461 | 2/1951 | Bay | 128/228 |
| 2,640,358 | 2/1953 | McClure | 222/416 X |
| 2,648,333 | 8/1953 | Cutter | 128/214 C |
| 2,704,544 | 3/1955 | Ryan | 128/214 C X |
| 2,786,467 | 3/1957 | Price | 128/214 D |
| 3,667,464 | 6/1972 | Alligood | 128/214 C |
| 3,949,745 | 4/1976 | Howell | 128/214 C |

FOREIGN PATENTS OR APPLICATIONS 21,724 9/1947 Finland ............... 137/135

*Primary Examiner*—Dalton L. Truluck
*Attorney, Agent, or Firm*—J. Harold Kilcoyne

[57] ABSTRACT

A parenteral fluid administration set comprising a container having therein a supply of a fluid to be administered intravenously and being characterized by a floating siphon operative to flow fluid from said container supply thereof at a predetermined rate of flow, said floating siphon comprising a float and at least one siphon U-tube whose shorter leg extends through and is affixed to the float and whose longer leg terminates below the inlet end of said shorter leg and a substantial distance above the container bottom, said longer leg opening to and flowing fluid into an axially non-rigid fluid-flow tube extending through the body of the fluid in said container and delivering same through the container bottom to an I.V. tubing line extending to an infusion needle, said axially non-rigid fluid-flow tube being fashioned from thin plastic or rubber sheet material and being radially collapsible under the pressure of the body of fluid acting thereagainst, but being maintained against complete radial collapse by a pliant coil spring extending through the non-rigid tube and whose coils possess the stiffness requisite to maintaining a fluid-flow passage through said non-rigid tube.

11 Claims, 3 Drawing Figures

U.S. Patent  Mar. 8, 1977  4,010,750
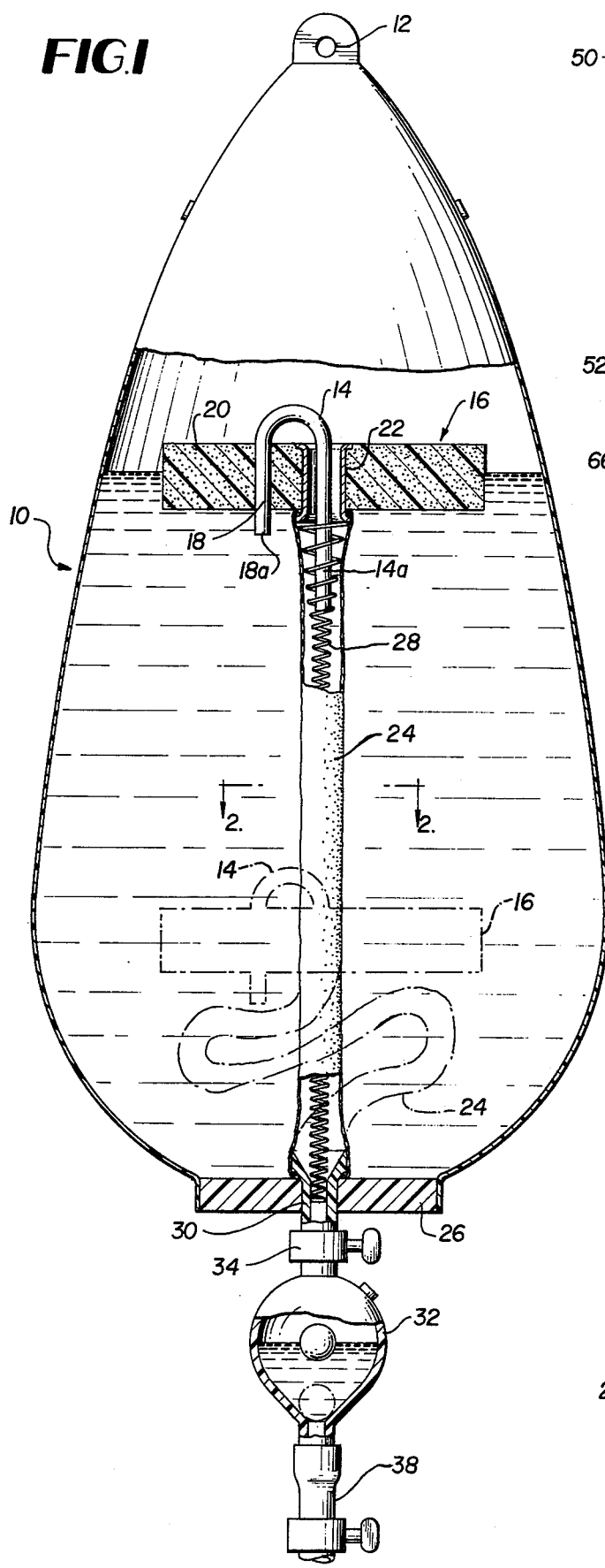
FIG.1
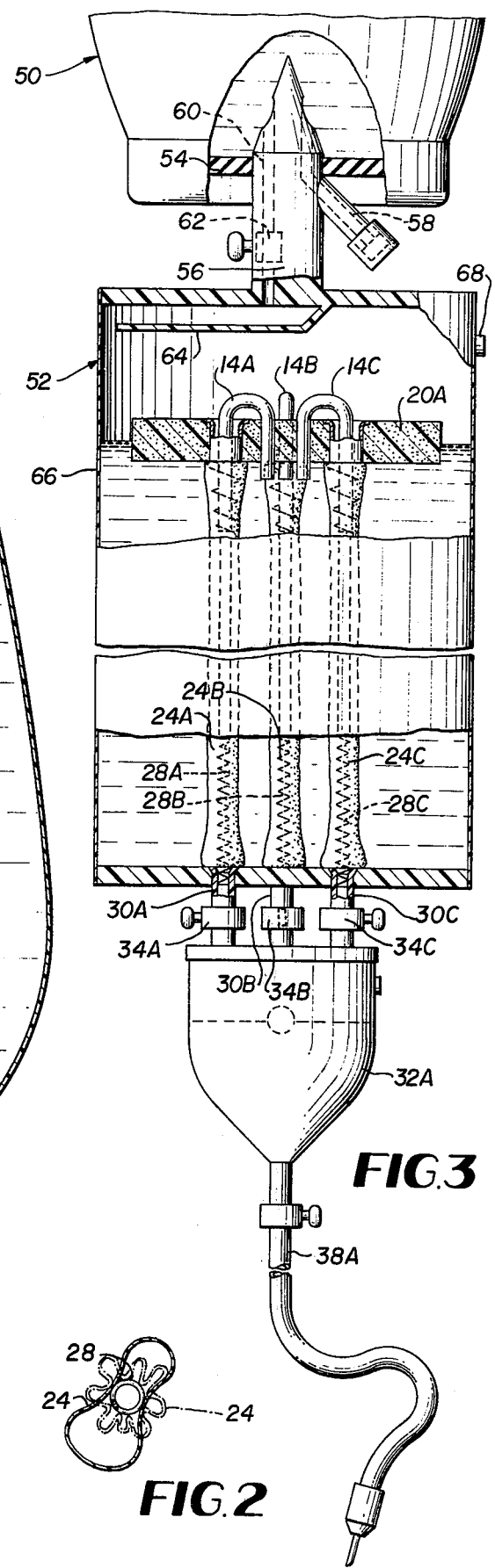
FIG.2
FIG.3

PARENTERAL FLUID ADMINISTRATION SETS

The Invention - In General

This invention relates to improvements in parenteral fluid administration sets of a design capable of dispensing parenteral fluid from a container (either a plastic bag or an inverted bottle) to tubing extending to an infusion needle at a controlled rate and with an accuracy comparable to that obtainable by power-driven units now in clinical use.

BACKGROUND OF THE INVENTION

My prior applications for U.S. Letter Pat. Ser. No. 608,576, filed Aug. 28, 1975, now U.S. Pat. No. 3,949,745 allowed Apr. 13, 1976, and Ser. No. 642365, filed Dec. 19, 1975, disclose and claim, among other features, parenteral fluid administration sets utilizing a floating siphon whose longer siphon leg operates within an upright open-ended rigid overflow tube and has length such that in certain positions of floating siphon travel, depending upon the level of the parenteral fluid in a container (which may be a flow regulator chamber connected to and receiving the parenteral fluid to be administered intravenously from an inverted bottle or similar type rigid container or a disposable plastic bag), its outlet end projects through and outwardly from the lower open end of said rigid overflow tube, said projecting end being provided with means for priming the siphon and/or for altering the calibre of the siphon.

While my aforesaid disclosed parenteral fluid administration sets are fully operative and effectively serve the purpose for which they were intended, recent experiments with variant devices have given indication that floating-siphon type administration sets employing a siphon U-tube whose longer leg is relatively short to the degree that its outlet end terminates a substantial distance above the bottom of said container and which further makes unnecessary the rigid overflow tube aforesaid, may constitute a practical and effective alternate construction, provided that in place of the rigid overflow tube, a fluid-flow tube fashioned of a material which renders the tube non-rigid axially and also radially collapsible under the pressure of the fluid content of the container in which said tube is immersed, with means for maintaining a flow path through said tube as the fluid level recedes, be utilized in place thereof.

OBJECTS OF THE INVENTION

A primary object of the present invention, therefore, is the provision of a clinically acceptable and effective parenteral fluid administration set characterized by a floating siphon-type flow regulating means wherein all positions assumed by said floating siphon, the longer leg of the siphon U-tube terminates a substantial distance above the fluid-container bottom and extends into and delivers the parenteral fluid into a flow-tube which extends through the body of fluid in the container and which is fashioned from a material rendering it both axially non-rigid with lowering of the floating siphon and collapsible radially under the pressure of the fluid in the container acting thereon along its immersed length.

Yet another object of the invention is the provision of a parenteral fluid administration set as last aforesaid and which further incorporates means insuring the maintenance of a flow path through the axially non-rigid and radially collapsible tube, in all positions assumed by the floating siphon.

Still another object of the present invention is the provision of a clinically acceptable fluid administration set operating on a principle which is equally adaptable to (i.e. usable with) either a plastic bag or the more conventional bottle source of the parenteral fluid to be administered.

A yet further object of the invention is the provision of a parenteral fluid administration set capable of dispensing the parenteral fluid to be administered in quantities which may increase in increments, from 25 cc's per hour to 175 cc's (total) per hour, for example.

DETAILED DESCRIPTION OF THE INVENTION

The above and other desirable objectives and features of the invention will become apparent from the following more detailed description thereof, taken with the accompanying illustrative drawing figures, wherein.....

FIG. 1 is a part-sectional view in elevation of one embodiment of the invention, i.e. a floating-siphon type of parenteral fluid administration set utilizing a plastic-bag source of the fluid to be administered, and wherein the floating siphon is the single siphon-tube type from whose longer outlet leg the fluid flows into the bore of an axially non-rigid, radially collapsible flow-tube.

FIG. 2 is a transverse section taken through an administration set according to the FIG. 1 embodiment which illustrates the action of a coil-spring means provided within the axially non-rigid, radially collapsible tube, to the bore of which the siphon delivers, for always maintaining a fluid-flow path therethrough.

FIG. 3 is a part-sectional view in elevation of another clinically acceptable embodimenet of the invention utilizing an inverted bottle source of parenteral fluid to be administered, and wherein a plurality (three) siphon tubes are utilized to provide flow rates which may vary in increments of 25 cc's from 25 cc's to 175 cc's per hour.

Referring to the so designated drawing figures in detail, FIGS. 1 and 2 are illustrative of a parenteral fluid administration set wherein the parenteral fluid to be administered is contained in a plastic bag 10 adapted to be suspended from its upper end which is shown to be provided with a grommet 12 for the reception of a bill of a hook or a suitable bracket arm (not shown). While following generally the structural details and principle of operation of the plastic bag-type parenteral fluid administration set disclosed in my application Ser. No. 642,365, filed Dec. 19, 1975, the fluid administration set of the present invention differs therefrom in that the longer leg 14a of the siphon U-tube 14 of the floating-siphon assembly generally designated 16, rather than having length such that in certain positions of the floating siphon it extends to and through the bottom of the plastic bag, instead terminates a substantial distance above said bag bottom, and more particularly terminates but a short distance below the inlet end 18a of the shorter siphon leg 18, which latter extends through and is affixed to the float component 20 of said floating siphon assembly 16.

FIG. 1 further illustrates that said float 20 is provided in its central area with a metal or plastic ferrule 22 having internal diameter which preferably is slightly oversize relative to the external diameter of said longer leg 14a of the siphon, thus providing ready accommodation for said longer siphon leg.

According to a further feature distinguishing the presently proposed administration set from my prior administration sets, an axially non-rigid flow-tube 24 (rather than a rigid open-ended overflow tube) into the bore of which the longer siphon leg 14a extends, is provided. Illustratively, said axially non-rigid flow-tube is affixed at its upper end to the float 20 (as by attaching its said upper end to the ferrule 22) and at its lower end to a rigid disc-form bottom member 26 with which the plastic bag may be provided.

The herein proposed administration set is also characterized by the aforesaid tube 24 being fashioned from a thin plastic sheet material such as "plastic wrap" or thin sheet rubber which, if not maintained against radial collapse, will collapse radially inwardly to bore-closing position under the pressure of the fluid content of the plastic bag 10 through which the tube extends. To prevent complete radial collapse as would block the flow of fluid there-through, the invention provides a coil spring 28 extending through and for the full length of the bore of the "plastic wrap" (or thin sheet rubber) tube 24, said spring being fashioned from a pliant material enabling it to adapt itself to the effective shortening of the "plastic wrap" tube 24 as the liquid level content in the plastic bag recedes, while at the same time possessing a coil stiffness radially as imparts to the spring the requisite strength in radial direction as to maintain a flow path through the "plastic wrap" tube open to the degree that the fluid flowing into its upper-end from the outlet end of the longer leg 14a of the siphon may flow freely along the full length thereof, ultimately to exit through a short-length outlet tube 30 which projects through the aforesaid bottom disc 26 and which in turn is connected and delivers fluid to a lower-level fluid reservoir 32, upon opening of a normally closed, open-shut type valve or clamp 34 carried by said short-length outlet tube 30. Said fluid reservoir 32 which is suitably vented in turn delivers to a length of intravenous tubing 38 terminating in an infusion needle (not herein shown), the latter corresponding to the fluid reservoir, IV tubing and infusion needle according to my aforesaid applications filed Aug. 28, and Dec. 19, 1975.

Illustratively shown in FIG. 1, suitable self-closing fluid inlet means 40 provided for the purpose of supplying the parenteral fluid to be administered to the interior of the plastic bag 10 and an inwardly opening vent 42 are provided in the plastic-bag wall, the latter vent preventing the formation of an air lock upon the fluid level in the container receding.

It is a further feature of the invention that the calibre of the bore of the siphon leg 14a will be pre-set to flow a predetermined quantity (say 50 cc's) of parenteral fluid per hour, there being thus no requirement of providing means for altering the calibre of the siphon tube. However, assuming a plurality (say three) siphons U-tubes being carried by one and the same float, each siphon longer-leg delivering fluid to a corresponding number of axially non-rigid "plastic-wrap" tubes, each corresponding to the aforesaid non-rigid tube 24 and each provided internally thereof with an elongated pliant but relatively radially stiff coil spring (corresponding to the aforesaid described axially extending and radially stiff coil spring 28), to be affixed in suspended relation to said single float, an administration set of the invention becomes capable of flowing fluid to and thence of dispensing same through three short-length fluid exit tubes (corresponding to the aforesaid single fluid exit tube 30) which project through the bottom disc 26 and deliver to a single fluid reservoir and thence through an IV line connected thereto and terminating in a single infusion needle. This latter feature is one of advantage and is highly desirable in that by pre-setting (pre-adjusting) the calibre of the three siphons to deliver the parenteral fluid in varying quantities, say in increments of 25, 50 and 100 cc's per hour, the utility of a parenteral fluid administration set as described is greatly enhanced.

Such an arrangement of a cluster of three siphon U-tubes, delivering to three non-rigid "plastic-wrap" tubes with their internal coil springs whose function is to prevent complete tube collapse, are shown in the FIG. 3 embodiment, wherein the fluid supply is from a conventional inverted bottle 50 (rather than a suspended plastic bag as in FIG. 1) to a flow regulator 52 corresponding to the flow regulator of my aforesaid U.S. Pat. No. 3,949,745.

More particularly, in the FIG. 3 embodiment, parenteral fluid flows from said bottle 50 upon its rubber stopper 54 being pierced by the point of a conventional piercing plug 56 which is more or less schematically shown to be provided with a one-way filtered air inflow passage 58 and an axial fluid outflow passage 60, which later is adapted to be opened and closed by a manually operable valve 62, the fluid flowing from the passage 60 being diverted sidewardly as by a diverter plate 64 affixed to the top closure of the cylindrical flow regulator 52 which may also provide the base flange of the piercing plug 56 from which said stopper-piercing point of said plug projects.

Preferably, the cylindrical wall 66 defining the flow regulator chamber is fashioned from deformable-reformable plastic material, whereby limited finger compression of said wall will initiate flow of the fluid contained in the regulator chamber through the siphon outlet legs to the interior of the "plastic wrap" tubes to which said siphon legs deliver.

Illustratively, the cylinder wall adjacent its upper end is provided with an air-flow opening 68 serving to prevent build-up of an air lock in the interior of the flow regulator chamber as the level of the fluid content therein recedes.

As earlier forecast, the bores of the three siphon U-tubes designated 14A, 14B, 14C are pre-set (chosen so as to be operative) to flow fluid in varying quantities, to their associated axially non-rigid and radially collapsible flow tubes 24A, 24B, 24C, and thence from the regulator chamber through short length outflow tubes 30A, 30B, 30C, (provided with open-shut type valves or clamps 34A, 34B, 34C) which deliver to a single fluid receiver 32A connected in the I.V. tubing line to an infusion needle (not shown). That is to say, one siphon U-tube bore may be of a size to dispense fluid at the rate of 25 cc's per hour, the second siphon U-tube bore at the rate of 50 cc's per hour; and the third U-tube bore at the rate of 100 cc's per hour. Accordingly parental fluid may be dispensed in quantities of 25 cc's per hour, or 50 cc's per hour, or 75 cc's per hour or 100 cc's per hour or 125 cc's per hour, or 150 cc's per hour or a total of 175 cc's per hour, depending on whichever rate is needed or considered desirable for the particular patient being infused, by the simple procedure of selecting the particular valve or clamp 34A-34C or combination thereof to be opened.

Thus, since the rate of fluid flow via an operatively open siphon (or siphons) U-tube will be uniform, an attending nurse need only adjust the flow from the inverted bottle 50 or equivalent container to the flow regulator 52 as insures a level of fluid therein on which the float 20A may float freely. In the event that any one or two of the three valves 34A, 34B, 34C is or are closed, with the third remaining open, the longer legs of all three siphons will continue to flow fluid into their fluid-flow tubes, the fluid accumulating in those from which the fluid-flow had been cut off. Thus, upon said one or two closed valves being reopened, fluid-flow through the previously closed off fluid-flow tube or tubes is immediately resumed, assuming of course that a proper level of fluid is present in the regulator chamber.

However, in connection with the just described feature of a fluid-flow tube continuing to accumulate fluid upon closing of its bottom open-shut type valve 34A (or 34B or 34C) it is to be observed that the upright conical shaping of the upper end of the coil spring 24 (which extends into and for a short length portion of said fluid-flow tube) and the corresponding conical shaping of the upper end of said fluid-flow tube (features best shown in FIG. 1), not only provide for the ready reception of the longer siphon leg but also insure against said flow tube accumulating fluid therein above a level which would prevent free venting of said fluid-flow tube through the ferrule opening in which the longer of the siphon-tube is accommodated.

Without further analysis, it will be appreciated that the described embodiments of the present invention satisfy the objectives thereof as set forth in the foregoing statement of its objects. However, it is to be understood that the invention is not limited to the precise structural details of said embodiments, since as pointed out herein such are illustrative and are to be understood as such.

Having described my present invention, I make the following claims therefor:

1. A parenteral fluid administration set comprising: a container having a bottom outlet and providing a supply of the parenteral fluid to be administered, a floating siphon adapted to follow the level of the fluid in said container and including a float and at least one siphon U-tube having a shorter and a longer leg, the shorter leg being affixed to and extending through the float body with its fluid-inlet end opening into the fluid in said container, the longer leg of the siphon U-tube extending through an aperture in the float, said longer siphon leg terminating a substantial distance above the container bottom, the fluid outlet end of said longer leg extending into and flowing fluid at a controlled rate to a flow tube affixed at its upper end to said float and at its lower end to said bottom outlet and which extends through the body of fluid in said container and is adapted to dispense said fluid flowing into same through the container bottom to an intravenous tubing line terminating in an infusion needle, said flow tube being fashioned from a material which renders it both non-rigid axially with lowering of the float and collapsible radially under the pressure of the fluid in the container acting thereon along its immersed length, and means disposed within and extending substantially the length of the tube for preventing its complete radial collapse as would block fluid flow through the tube.

2. A parenteral fluid administration set according to claim 1, wherein said container takes the form of a plastic bag having means for suspending same from its upper end.

3. A parenteral fluid administration set according to claim 1, wherein said means for preventing complete radial collapse of the axially non-rigid tube under the pressure of the fluid in the container effective thereagainst comprises a pliant coil spring extending the length of the flow tube and being capable of adjusting itself to axial shortening of said the flow tube while at the same time maintaining its own bore open, thereby to provide a fluid flow-path through the collapsed flow-tube.

4. A parenteral fluid administration set according to claim 3, wherein said coil spring adjusts itself to axial shortening of the axially non-rigid tube by assuming a serpentine configuration and causing the non-rigid tube to follow such configuration.

5. A parenteral fluid administration set wherein according to claim 1, wherein said axially non-rigid flow-tube is fashioned from a thin plastic material.

6. A parenteral fluid administration set according to claim 1, wherein the outlet end of the longer leg of the siphon has fixed calibre which is such as to flow a predetermined known quantity of fluid per hour to said axially non-rigid flow tube and thence to a receiving reservoir in said I.V. tubing line.

7. A parenteral fluid administration set according to claim 6, wherein the axially non-rigid tube delivers fluid to said receiving reservoir via a short length exit tube mounting an open-shut type valve means disposed thereon below the bottom of the container.

8. A parenteral fluid administration set according to claim 7 wherein plural siphons, axially non-rigid radially collapsible flow-tubes to which the outlet legs of the siphons deliver and means for preventing complete radial collapse of said flow-tubes are carried in suspended relation from a common float and the siphon outlet legs have calibre such as to flow fluid to the short-length exit tubes in quantities of 25 cc's, 50 cc's and 100 cc's per hour, respectively.

9. A parenteral fluid administration set accroding to claim 1, wherein the fluid container comprises an inverted bottle supplying the fluid to be administered to the chamber of a plastic-walled fluid regulator in which at least said one floating siphon U-tube, axially non-rigid and radially collapsible flow-tube and means for insuring against complete radial collapse of said flow-tube are operative as aforesaid.

10. A parenteral fluid administration set according to claim 9, wherein the wall defining said chamber is fashioned from a deformable-reformable plastic capable of being compressed by finger squeeze pressure applied thereto and when compressed and released, initiating flow through the siphon U-tube.

11. A parenteral fluid administration set according to claim 10 wherein three siphon U-tubes, three axially non-rigid, radially collapsible flow-tubes including means for preventing complete radial collapse of said flow-tubes are suspended from a common float and wherein the calibres of the outlet ends of the siphon tubes are such as to dispense fluid from the supply thereof in the flow regulator chamber in quantities of 25 cc's, 50 cc's and/or 100 cc's per hour, respectively.

* * * * *